United States Patent [19]
Roarty et al.

[11] Patent Number: 5,323,429
[45] Date of Patent: Jun. 21, 1994

[54] ELECTROCHEMICAL MONITORING OF VESSEL PENETRATIONS

[75] Inventors: David H. Roarty, Murrysville, Pa.; David A. Eden, Manchester, United Kingdom

[73] Assignee: Westinghouse Electric Corporation, Pittsburgh, Pa.

[21] Appl. No.: 4,823

[22] Filed: Jan. 15, 1993

[51] Int. Cl.$^5$ .............................................. G21C 9/00
[52] U.S. Cl. .................................... 376/249; 376/305
[58] Field of Search ....................... 376/305, 245, 249; 204/153.11, 404; 324/425, 71.2, 71.5

[56] References Cited

U.S. PATENT DOCUMENTS

| | | | |
|---|---|---|---|
| 2,834,858 | 5/1958 | Schaschi | 201/63 |
| 3,491,012 | 1/1970 | Winslow, Jr. | 204/195 |
| 3,504,323 | 3/1970 | Meany, Jr. | 338/13 |
| 4,425,193 | 1/1984 | Taylor | 204/1 T |
| 4,426,618 | 1/1984 | Ronchetti et al. | 324/65 CR |
| 4,548,785 | 10/1985 | Richardson et al. | 376/249 |
| 4,575,678 | 3/1986 | Hladky | 324/425 |
| 4,655,077 | 4/1987 | Purvis et al. | 73/86 |
| 4,759,902 | 7/1988 | Anstine | 376/306 |
| 4,831,324 | 5/1989 | Asakura et al. | 324/57 R |
| 4,935,195 | 6/1990 | Palusamy et al. | 376/249 |
| 5,139,627 | 8/1992 | Eden et al. | 204/153.11 |
| 5,171,517 | 12/1992 | Solomon et al. | 376/245 |

FOREIGN PATENT DOCUMENTS

| | | |
|---|---|---|
| 0052388 | 5/1982 | European Pat. Off. . |
| PCTGB8700-310 | 11/1987 | PCT Int'l Appl. . |
| PCTGB8700-500 | 2/1988 | PCT Int'l Appl. . |
| 2118309 | 10/1983 | United Kingdom . |

OTHER PUBLICATIONS

"On-Line Materials Surveillance for Improved Reliability in Power Generation Systems," Paper No. 254, NACE Annual Conference and Corrosion Show, Mar. 1991.

Primary Examiner—Donald P. Walsh
Assistant Examiner—Meena Chelliah

[57] ABSTRACT

Stress-corrosion damage is monitored in penetrations traversing the wall of a vessel containing an electrolyte, such as a nuclear reactor pressure vessel containing a coolant. The vessel wall has tubular penetrations for coupling external devices to internal structures of the vessel while maintaining a pressure barrier, such as control rod guides and sensor signal cables. The penetrations are subject to stress-corrosion damage, especially adjacent welds affixing the tubes to the vessel head. One or more of the penetrations is provided with a probe forming with the tube an electrochemical sensor cell, including an electrode exposed to the electrolyte together with the surface of the penetration. The electrode and the surface are otherwise insulated, and a plurality of electrodes can be arrayed for monitoring distinct localized areas. The electrodes are wired to a detector circuit developing signals as a function of electrochemical activity due to stress and corrosion, indicative of corrosion of all the penetrations. Electrochemical potential, impedance, current, and particularly noise levels in these signals are detected and read out for assessing deterioration of the penetration surface as a function of the electrochemical activity.

17 Claims, 2 Drawing Sheets

1

ELECTROCHEMICAL MONITORING OF VESSEL PENETRATIONS

BACKGROUND OF THE INVENTION

1. Field of the Invention

This invention relates to the field of corrosion assessment in a metal by monitoring electrical activity between the metal and an electrode, both being subjected to an electrolyte. More particularly, the invention concerns monitoring localized corrosion of circular structural penetrations of vessels, for example the structures penetrating the vessel of a nuclear reactor for coupling control and sensing devices through a vessel wall.

2. Prior Art

There are various reasons for providing structures penetrating vessels, such as a conduit attached to an opening in the vessel at one or more welds. The conduit may be arranged, for example, to provide a flow path, to pass a mechanical device, or to couple electrical conductors through a vessel wall. Where the vessel contains an electrolyte and is subject to thermal and/or mechanical stress, the penetration structure is subject to corrosion. Where an asymmetric weld or similar structure affixes a penetration to a pressurized vessel containing an electrolyte, corrosion-stress cracking can be a problem, particularly in the area of the attachment of the penetration structure to the vessel.

A pressurized water nuclear reactor vessel is an example. A pressurized water nuclear reactor comprises a pressure vessel containing nuclear fuel and a conduit system whereby a coolant such as water or water containing cobalt is fed into and out of the vessel. The fuel comprises a plurality of long vertical rods that are closely spaced and interspersed with control rods that are movable into the spaces between the fuel rods to damp a selected proportion of nuclear flux and thereby control the rate of nuclear decay of the fuel as well as the amount of heat generated. The coolant is fed to the bottom of the vessel, flows upwardly over the fuel rods and exits at a level above the fuel rods, being heated in the process. The coolant is heated to a high temperature (e.g., 600° F.) and develops substantial pressure (e.g., 2,200 psi).

Instrumentation and control devices are mounted in and on the reactor vessel to ensure proper operation. Although it is possible to provide penetrations of the reactor vessel wall at various places to accommodate the mechanical and electrical couplings needed for these devices, it is preferable to place the penetrations at the top of the vessel and thereby provide higher integrity at the bottom, for improved safety characteristics. Typically, the reactor vessel comprises a generally cylindrical hollow body of relatively thick steel (e.g., about 13 cm or 5 inches) with a lid or reactor vessel head attached at the top to define a sealed pressure vessel. Penetrations for mechanical and electrical couplings across the pressure boundary are provided in the form of fittings that extend through the head or lid of the reactor vessel.

Penetrations of the vessel head are provided, for example, to accommodate movable control rod guide devices, and to pass conductors that couple electrically to sensors located inside the vessel, such as temperature and nuclear flux level sensors disposed in thimble tubes interspersed among the fuel rods. The tubes or similar structures penetrating the head may terminate flush with the inside wall of the head or may protrude into the internal volume. They may also traverse the plane of the head perpendicularly or at an angle. Typically, the penetration tubes are aligned vertically, parallel to one another and in alignment with the fuel rods. The control rods, for example, can thereby be engaged by actuators that are movable upwardly or downwardly in the penetration tubes, to accomplish corresponding displacement of the control rods relative to the fuel.

Whether movable or static, the structures passing through the vessel head have associated penetration tubes that are arranged to withstand the pressure developed by the coolant and to maintain a pressure boundary. The penetration tubes extend through the vessel head and include pressure fittings adapted to pass the control rod mechanisms or electrical signal couplings, respectively. The collection of penetrations and couplings are known as the reactor vessel head adaptor.

All the tubing and conduits of the reactor which carry the coolant are subject to corrosion over time. There are a number of reasons for such corrosion, including chemical reaction with the coolant (which is an electrolyte), the effect of nuclear radiation, mechanical stresses due to temperature and pressure variations, etc. Penetrations of the reactor vessel head are subject to stress-corrosion cracking, leading to potential leakage.

The vessel head is dome shaped, as appropriate for withstanding pressure. Whereas the penetrations typically are vertical and the head is a dome, those penetrations which are radially spaced from the center of the dome pass through the dome at an angle relative to a tangent to the dome surface. Welds which attach the penetration tube to the vessel head are therefore not placed at the same axial level on the penetration tube, and/or are characterized by different sized weldments on opposite sides of the tube. This is especially pronounced at the penetrations located at the outer radius of the vessel head. Thermal stresses are created by the welds for this reason. The thermal stresses further subject the penetration tubes to stress-corrosion cracking, and potential leakage of coolant as a result of through-wall stress corrosion cracking of the tubes, particularly in the area adjacent axially spaced or differently sized welds.

It would be beneficial to monitor cracking at vulnerable locations such as the vessel head penetrations in an on-line and automated manner, to determine when actual crack propagation is taking place and to assess the effectiveness of corrective measures taken to arrest corrosion of the reactor vessel. An on-line crack monitoring system could also provide information to evaluate the relative severity of corrosion at different locations in the reactor head to help determine and correct the root causes.

Electrochemical corrosion measurements have been taken to generally monitor the level of corrosion of metals that are exposed to an electrolyte. In high temperature environments such as boilers, corrosion may be encountered due to exposure to flue gases or to an aqueous coolant. U.S. Pat. No. 4,575,678—Hladky discloses a general method for analyzing deterioration of metal structures carrying electrolytes, for example, a pipe or conduit, a storage tank, process vessel, heat exchanger, pump or valve. An electrochemical probe intended for ongoing collection of corrosion data, that protrudes from a vessel wall into the electrolyte, is disclosed for example, in international application PCT/GB87/00500—Cox et al. A probe that is structured to form a section of conduit through which the electrolyte passes is disclosed in U.S Pat. No. 4,426,618—Ronchetti et al. In each case, the probe comprises a plurality of corrosion sensing electrodes that are exposed to the electrolyte. The electrical potentials of the electrodes and the current passing between the electrodes is sensed and related to the extent of chemical corrosion of the electrodes. Corrosion of the electrodes is comparable to corrosion of the vessel, conduit or other structure that holds the electrolyte. Therefore, by sensing the level of corrosion of the electrodes and integrating the results, the probe can be used to estimate the instantaneous rate of corrosion of the structure as a whole. Such information can be incorporated as a part of a maintenance program as disclosed in U.S. Pat. No. 4,935,195—Palusamy et al.

Specific sensing and monitoring for electrochemical resistance, galvanic current between electrodes, electrochemical potential noise and electrochemical current noise are disclosed for measuring the deterioration of a combustion vessel in "On-Line Materials Surveillance for Improved Reliability in Power Generation Systems," Paper No. 254, NACE Annual Conference and Corrosion Show, March 1991. Electrode structures which are useful for such monitoring are disclosed, for example, in U.S. Pat. Nos. 3,504,323—Meany, Jr.; 3,491,012—Winslow, Jr.; and 2,834,858—Schaschl. These teachings and these patents, and the foregoing patents to Palusamy and Hladky, are hereby incorporated in their entireties.

The present invention is intended to apply the art of electrochemical monitoring to the specific problems of penetration structures traversing the walls of vessels, and is particularly applicable to monitoring localized corrosion of penetrations traversing a wall of a nuclear reactor vessel. It has been discovered according to the invention that by instrumenting a subset of a plurality of penetrations of a vessel or similar electrolyte-holding structure, in particular the control and instrumentation penetrations of a nuclear reactor vessel head, one can assess the status of the penetrations generally, and thereby obtain information on this critical area of the reactor. Furthermore, the corrosion characteristics of particular areas of the penetration tubes can be selectively monitored, for distinguishing corrosion occurring at different locations in the penetration tubes.

The invention is useful for assessing present corrosion level, status and integrity of the vessel penetrations, and for providing information whereby the useful life of penetration structures can be decremented for planning and executing required maintenance steps.

SUMMARY OF THE INVENTION

It is an object of the present invention to enable on-line monitoring of stress-corrosion cracking associated with vessel penetrations, i.e., structures that couple through the wall of a vessel, conduit or similar structure carrying an electrolyte.

It is a further object of the invention to use at least one exemplary structure penetrating a vessel as one of the electrodes of an electrochemical sensor, for assessing deterioration of a plurality of such penetrating structures due to chemical and mechanical stress on the structures.

It is another object of the invention to sense for corrosion at different locations on the inside or protruding outside wall of a vessel penetration, for example at different axial positions and circumferential positions around penetration having a circular cross section.

It is also an object of the invention to assess the deterioration of vessel penetrations by electrochemical monitoring of a subset of the penetrations using an on-line data collection system.

It is another object of the invention to monitor the penetrations of a nuclear reactor head adaptor at critical or vulnerable locations, particularly by instrumenting circular penetrations at and adjacent passage through a vessel head structure at an angle relative to the plane of the head.

These and other aspects are found in the stress-corrosion damage monitoring method and apparatus according to the invention. Stress-corrosion damage is monitored in the penetrations traversing the wall of a vessel containing an electrolyte, such as the penetrations of the head adaptor of a nuclear reactor vessel containing a coolant and nuclear fuel. The vessel wall has a number of tubular penetrations for coupling mechanical or electrical external devices to internal structures of the vessel while maintaining a pressure barrier, such as control rod guides and sensor signal cables. The penetrations are subject to stress-corrosion damage, especially at and adjacent the passage through the head, where the penetrations may be welded or similarly attached to the vessel head in a manner generating thermal stresses. One or more of the penetrations is provided with at least one, and preferably a plurality of electrodes that define electrochemical sensor cells. A series of electrode pairs detect corrosion activity on the surface of the penetration tube material, primarily the areas most nearly adjacent the respective electrodes of the probe, making it possible to distinguish between corrosion levels at different positions on the probe. The electrodes of each pair represent a working electrode and a reference electrode. The corroding surface of the penetration tube nearby the pair represents another working electrode. These electrodes are exposed to the electrolyte, as is the corroding wall of the penetration. The electrodes and the corroding wall are otherwise electrically insulated, and are wired to a detector circuit developing signals as a function of electrochemical activity due to stress and corrosion. Electrochemical potential, impedance, current, and particularly noise levels in the potential and current signals are detected for each pair of electrodes and each distinguishable monitored area of the corroding tube. The signals are analyzed and/or read out for assessing deterioration of the penetration wall as a function of the electrochemical activity. In this manner, the condition of all the vessel penetrations is assessed in a manner that enables identification of areas of the penetrations where corrosion is occurring preferentially, facilitating appropriate corrective action when necessary.

BRIEF DESCRIPTION OF THE DRAWINGS

The invention can be appreciated with reference to preferred embodiments and examples set forth in the following discussion and shown in the drawings. It should be appreciated, however, that the drawings and the discussion are intended as exemplary rather than limiting, and the invention is capable of variation within the scope of the subject matter claimed. In the drawings.

DETAILED DESCRIPTION OF THE PREFERRED EMBODIMENTS

Figure 1:
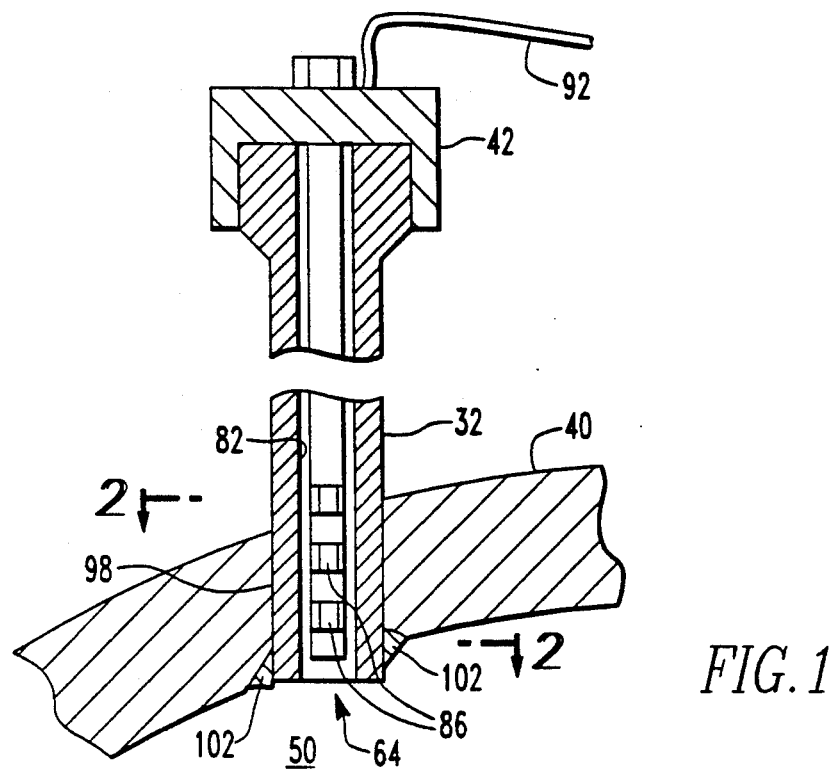
FIG. 1 is a partial section view through a reactor vessel head, showing a corrosion monitoring probe mounted in a penetration tube according to the invention.

Referring to FIG. 1, a tubular conduit 32 traverses a wall 40 of the reactor vessel of a nuclear reactor, and is subject to stress-corrosion damage due to chemical reaction with the coolant and due to mechanical stresses caused by variations in thermal expansion and pressure. The penetration 32 shown can be one of a plurality of penetrations that traverse the reactor head package, and define pressure fittings 42 whereby mechanical means such as control rod guides and electrical means such as signal lines pass through the pressure barrier between the reactor vessel and the containment building (not shown). The penetrations 32 to be monitored are the conventional pressure sealing penetration tubes otherwise used for the control rod guides, signal lines and the like. At least one of the penetration tubes 32, and preferably a characteristic sample or subset of the penetration tubes is instrumented as a means to assess corrosion of the sample tubes, and also to estimate the corrosion of comparable tubes which are not similarly instrumented.

The reactor vessel, which is not shown in detail, is arranged to enclose a quantity of nuclear fuel and a coolant to pass over the fuel for carrying away heat. The coolant normally is water, forming an electrolyte 50 with various ions in solution. The penetrations 32 define conduits subject to stress-corrosion damage due to operation of the nuclear reactor. Although the penetrations 32 are partly exterior to the reactor vessel, they are subjected to chemical action from the coolant or electrolyte 50 as well as stress due to temperature and pressure conditions.

Like most metals subjected to such conditions, the walls of the penetrations corrode and can become cracked over time. According to the invention, the ongoing extent of such corrosion is assessed. Information gathered in this manner can be used to track the accumulated corrosion of the penetration tube walls for planning maintenance, and also is useful for detecting conditions of increased stress and corrosion, especially at distinct areas which are vulnerable due to the techniques by which the penetration tubes are attached to the reactor vessel head. As appropriate, the results of the monitoring may involve taking actions to decrease the rate at which the corrosion occurs, e.g., adjusting the chemical makeup of the coolant, or actions to replace or repair penetration tubes which are failing or subject to impending failure.

For assessing corrosion, the chemical reactions affecting the penetration wall are detected electrically. At least one electrochemical sensor arrangement or cell 60, and preferably an array 64 of sensors, is mounted in at least one of the penetrations 32 traversing the reactor wall 40. Each sensor cell 60 has a working electrode 72 and a reference electrode 74, insulated from one another and from the wall 82 of the respective penetration tube 32. The working electrode 72 and the reference electrode 74 are placed immediately adjacent an area of the penetration wall 82 to be monitored, the respective cell responding substantially to corrosion in that area. The penetration wall 82 and the electrodes 72, 74 are exposed commonly to the electrolyte 50 during operation of the nuclear reactor.

In the preferred embodiment, separately wired electrodes are positioned at different places on the surface of the sensor probe, for monitoring corrosion at a plurality of distinct areas. Axially spaced groups 86 of circumferentially spaced electrode arrays 88 allow separate monitoring of areas around the sensor probe. For example, for monitoring corrosion in the area of passage through the vessel head, which is about 13 cm or 5 inches thick, three to five axially spaced sets of eight circumferentially spaced sensing electrodes can be provided. This arrangement provides for 24 to 40 separately distinguishable corrosion monitoring areas on the internal wall of the penetration tube. It would also be possible to mount an array of sensing electrodes so as to encompass the outer surface of a penetration tube that protrudes into the reactor vessel. However, the exemplary embodiments shown are arranged to monitor corrosion from the inside of the penetration tube, specifically in the area of its attachment to the vessel head, where stresses on the penetration tube make corrosion a problem.

Figure 3:
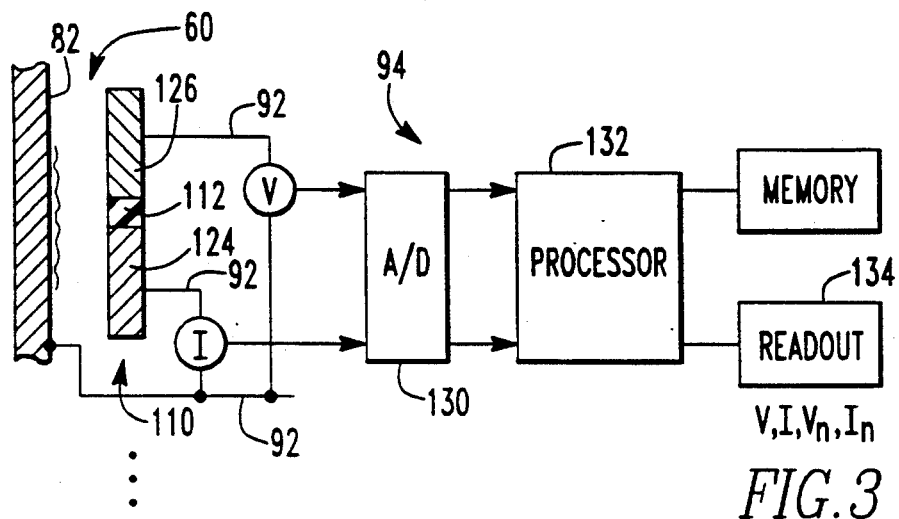
FIG. 3 is a schematic electrical diagram illustrating the input and outputs generated according to the invention for corrosion monitoring, showing only one set of electrodes for purposes of simplicity; and, FIG. 4 is a schematic elevation view illustrating instrumenting a reactor head package with a plurality of corrosion monitoring probes.

The respective electrodes are coupled via signal lines 92 to instrumentation as shown in FIG. 3 for capturing potential and current information and analyzing the data to determine the extent of potential and current noise. The signal lines 92 are routed out of the penetration via a standard pressure fitting 42 operable to maintain the pressure boundary. The signal conductors 92 couple to a detector circuit 94 the voltage and current signals developed at the electrodes 72, 74. The penetration wall 82 is also coupled to the detector circuit for coupling the wall as a working electrode to the detector. The voltage and current signals vary as a function of electrochemical activity leading to stress-corrosion damage of the penetration wall. The extent of corrosion is a function of exchange currents that pass between the electrodes and the electrolyte and produce current and voltage signals between the respective sections of the penetration wall and the electrodes associated therewith.

The detector circuit 94 is coupled to the signal conductors 92 and is operable to encode data representing at least one of electrochemical potential, electrochemical impedance, and current passing through the electrolyte between the electrodes and the wall 82. Preferably, the current and voltage noise levels in these signals are assessed. The data thereby developed is read out for assessing deterioration of the penetration wall as a function of the electrochemical activity.

There are a number of specific components of electrical activity that can be used to reflect the extent of corrosion of a metal in an electrolyte, and reference can be made to the disclosures mentioned in the foregoing prior art section of the Specification for specific examples, which are hereby incorporated in their entireties. Briefly, the signal conductors 92 are preferably coupled to measurement circuits operable to amplify and encode the electrical potential levels and current dissipation through the wall, the electrode and the electrolyte, which signals are representative of the level of corrosion and the extent of stress-corrosion damage which is accumulating. Some parameters which can be monitored include electrochemical impedance as a function of frequency, galvanic current between the electrode and the wall, electrochemical potential noise and electrochemical current noise.

Electrochemical impedance is measured by analyzing the response of the corrosion interface to an applied sinusoidal potential waveform over a range of frequencies, e.g. 0.1 Hz to 10 KHz. This gives information on the resistance/capacitance characteristics of the corroding surface. At the higher frequencies, the impedance can be related to the solution resistance of the electrolyte in the circuit including the penetration wall and the electrode, and can also be related to the extent of accumulated scale and/or similar deposits that are present. The response at lower frequencies can be related to the polarization resistance (or DC impedance value) of the sensor circuit. By subtracting the solution resistance, an accurate representation of the resistance to charge transfer at the corrosion interface can be determined. A lower charge transfer resistance indicates a higher rate of corrosion, and vice versa.

Zero resistance ammetry can be used to determine the galvanic current between two electrodes, in this case between the penetration wall and the electrode therein. Normally, the penetration wall and the electrode are of dissimilar metals, which inherently produce a galvanic current when coupled as a cell. This technique can also determine the galvanic current between nominally identical electrodes, which typically are at least different enough to take up slightly different potentials. When the penetration wall and the electrode are coupled via a zero-resistance ammeter, a measurable current flows. The DC value of the coupling current during active corrosion is proportional to the level of corrosion activity then in progress on the electrodes.

Electrochemical potential noise is a low level random fluctuation of the electrochemical corrosion potential. The fluctuation is typically of a low amplitude (e.g., less than a millivolt), and a low frequency (e.g., 1 Hz and lower). By measuring the low frequency variation in the electrochemical potential, a time varying signal can be developed that can be correlated against the mode of corrosion attack. For example, pitting corrosion and crevice attack produce clearly distinct signatures in measured electrochemical potential noise.

Electrochemical current noise can also be measured. The current noise is similar to the potential noise, except that fluctuations in the coupling current between similar electrodes are recorded and analyzed. An estimate of the overall rate of corrosion can be made from the electrochemical current noise output signal after calibrating the sensor cell empirically, using controlled weight loss exposure measurements.

The penetration tube 32 comprises a tubular conduit traversing a wall defined by the head structure 40 of the reactor pressure vessel. The conduit is circular in cross section and is fitted closely into a bore 98 in the vessel head 40. The vessel head is dome shaped. However, the penetration tubes 32 are parallel to one another. As a result, the longitudinal axes of the penetration tubes are disposed at an angle relative to the plane of the wall of the head structure 40 at the penetration 32. As shown in FIG. 1, a result is that the welds 102 which attach the penetration tube 32 to the vessel head 40 are of different sizes and are disposed at different axial positions along the penetration tube 32. The penetration tube 32 can protrude inwardly of the vessel wall, as also shown in FIG. 1. As a result of this mounting arrangement, the penetration tube 32 is especially subject to stress-corrosion cracking adjacent the welds 102, namely in the area where the penetration tube 32 traverses the vessel head 40. The electrodes 72, 74 of the sensing cells 60 are preferably located in this area, where the penetration tube is vulnerable.

Figure 4:
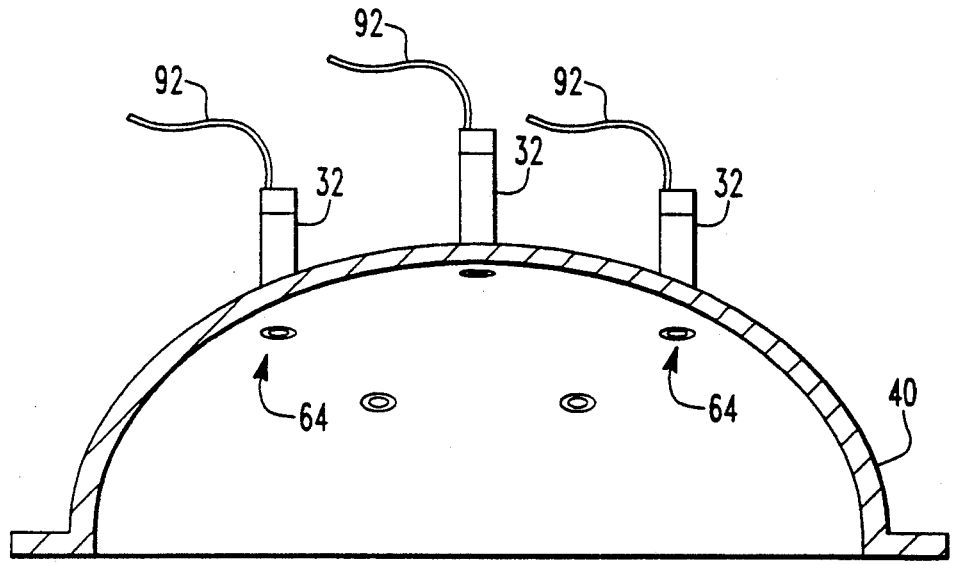

The penetration 32 used for corrosion monitoring is similar to the other penetrations in the head structure 40 of the reactor pressure vessel. As a result, corrosion of the penetrations generally can be assessed by measuring the corrosion occurring at the instrumented penetration. At least one penetration is instrumented; however it is also possible to instrument a plurality of penetrations as shown in FIG. 4, for separately assessing corrosion at different positions of the vessel head. For example, the instrumented penetrations can be disposed diametrically opposite one another or otherwise spaced around the circumference of the head package, and/or placed at different radial distances from the centerline of the reactor vessel. The instrumented penetrations are provided with pressure fittings 42 in the same manner as the penetrations used for control rod guides or signal lines for other sensors, such as temperature, pressure, nuclear flux and the like.

Figure 2:
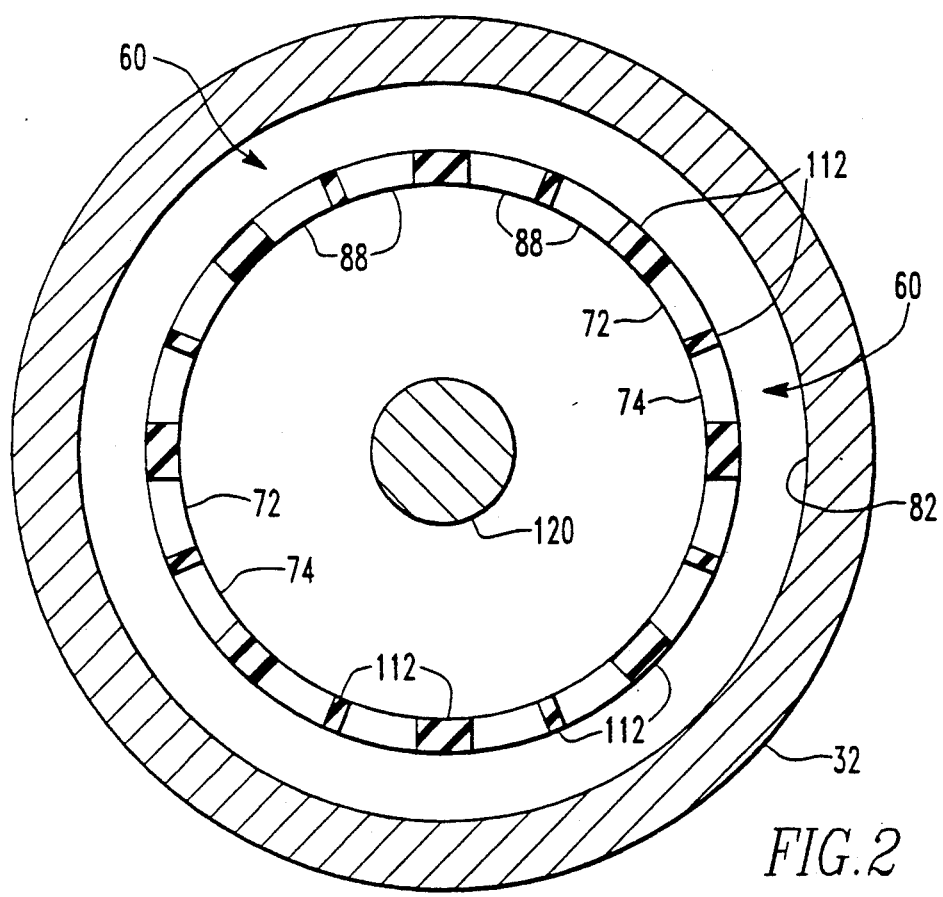
FIG. 2 is a section view through the probe in the area of the passage of the penetration through the reactor vessel head, taken along lines 2—2 in FIG. 1, and showing a circumferential distribution of paired electrodes.

Referring to FIGS. 1 and 2, a plurality of paired electrodes 72, 74 are arranged around the circumference of the probe at axially spaced levels 86. The two electrodes 72, 74 of each pair 110 interact through the electrolyte 50 primarily with the nearest portion of the wall of the penetration tube 32, allowing the arrayed electrodes to develop signals specific to distinct areas. Electrical insulators 112 are interspersed between the electrodes in the probe, the electrodes and insulators being mounted on a supporting post 120 or spring mounting, for example as in the probe of international patent application PCT/GB87/00500.

Accordingly, the penetration tube 32 is used as one of the working electrodes for each measurement. The two counter electrodes 72, 74 are positioned along the tube in the vicinity of the potential cracking site, preferably where stresses are highest, e.g., due to the mounting of the penetration tube. As shown schematically in FIG. 3, the current signal is sensed between one electrode 124 and the penetration wall to obtain the coupling current and current noise signals. The voltage signal is sensed between the other electrode 126 and the penetration wall as the other electrode to develop the potential reference signal and potential noise signal. These signals are coupled to digitizing means 130 operable to sample the data, and to a processor 132 that analyzes the sample data numerically.

The electrodes used for voltage and current measurements can be fabricated from the same material as the tube. Multiple electrodes can be installed within the penetration tube for any or all of the measurements, e.g., with electrode sets 110 disposed 180° apart around the circumference or spaced by 45° as shown, to detect variations in the corrosion conditions around the inside circumference of the tube, and/or at different axial positions. The specific arrangement of the electrode pairs can be varied with the type and dimensions of the penetration, and with the extent of local area monitoring desired. Similarly, one or a plurality of penetration tubes 32 traversing the vessel head can be instrumented in this manner as shown in FIG. 4, to obtain complete data respecting corrosion of the penetration tubes.

Using electrochemical noise measurement to assess stress-corrosion cracking and similar corrosion of the reactor vessel penetrations has several advantages. The probe design can be extremely simple and rugged. Therefore, the probe readily qualifies as safe in the severe environment of the reactor vessel, and reliable long-term measurements can be expected.

The electrochemical noise measurement technique is also quite accurate, being capable of detecting crack initiation before visually detectable damage can occur. The technique also detects crack propagation, enabling estimates of crack depth. Since analyzing the noise signal effectively measures the free corrosion potential of the penetration wall and the electrode(s), no polarization of the specimens is required, which could potentially accelerate the corrosion process by providing energy for ion exchange. Analysis of the noise signals not only allows the level of corrosion to be assessed, but also helps to identify the fundamental electrochemical and corrosion processes at work. This information is critical for root cause analyses and failure studies. Finally the technique is excellent for monitoring complex localized corrosion events such as the typical stress-corrosion cracking experienced in reactor vessel penetrations 32 in the area of the reactor vessel wall 40.

The circuitry needed to capture and analyze the signals developed from the sensors can include high input impedance amplifiers coupled to data processing means operable to analyze the data for frequency specific data. Preferably, the outputs of the device are coupled to suitable display and/or readout devices for graphic, tabular, summary reporting, and potentially for the triggering of maintenance alarms. The data is also stored for reference, and can be communicated remotely via modem or other communication means. An integrated package of circuitry specifically for electrochemical noise analysis that can be applied to the measurements taken according to the invention is available from CAPCIS MARCH, Limited (CML), Manchester, UK, under the product name DENIS (an acronym for Digital Electrochemical Noise Integrated System).

The probe is coupled to the data acquisition and analysis circuitry in the same manner as other process monitoring variables generally. Various intermediate and ultimate elements such as sampling analog to digital converters, multiplexers, cables and other signal lines, data acquisition equipment, and electrochemical noise analyzers can be provided. Preferably, electrochemical noise analysis is employed via software running on a processor coupled to process the data, and the software can include maintenance predictive functions for estimating the remaining useful life of the penetration tubes.

The probe is preferably dimensioned and arranged to be compatible with an existing type of reactor head adaptor tube, and preferably is a unitary structure that can simply be inserted in the penetration 32, sealed by the pressure fitting 42 and wired to the detector circuits 94 for operation. The electrode array placed within the tube can be located in the tube internal diameter near the location where cracking has been observed in penetration tubes of this type, namely in the area adjacent the junction with the reactor walls. The probe pressure boundary qualification is also an important concern. Preferably, an end cap design or similar configuration similar to the pressure closures used with existing sensing cable arrangements is employed. The probe is fabricated in accordance with applicable regulatory Code requirements and using Code materials as applicable.

The probe is a durable device, comprised substantially of solid metal materials for the support and the electrodes, coupled via electrical insulation 112 so as to maintain electrical isolation of the tube 32 and the electrodes except via ionic current flow through the electrolyte 50. As installed in the head adaptor tube and utilizing suitably durable materials for the probe, its insulating materials and pressure fittings, the probe does not compromise plant safety margins with respect to loads such as pressure, temperature, seismic shock, flow vibration, etc. Thus the probe can be arranged to survive the effects of radiation exposure over a design life that at least exceeds the specifications applicable to the respective penetration tube 32.

Preferably, the monitoring system is operated on a continuous basis during normal operation of the plant. Data analysis software provides a continuous on-line indication of corrosion activity for operation monitoring and for maintenance planning purposes.

The invention having been disclosed, variations will now be apparent to persons skilled in the art. Whereas the invention is intended to encompass not only the foregoing specific embodiments but a range of equivalent variations as well, reference should be made to the appended claims rather than the foregoing examples, in order to assess the scope of the invention in which exclusive rights are claimed.

We claim:

1. A method for assessing deterioration of penetrations traversing a vessel wall of a nuclear reactor pressure vessel defining an enclosure for an electrolyte, comprising the steps of:
   instrumenting at least one of the penetrations by installing a probe, the probe having a plurality of electrodes disposed in an array and positioned adjacent and electrically insulated from metal defining a penetration wall, the probe including conductors coupled individually to respective ones of the electrodes and a conductor coupled to the metal defining the penetration wall such that the penetration wall functions as a working electrode at distinct positions adjacent the respective electrodes;
   exposing both the electrode and the penetration wall to the electrolyte in the enclosure;
   monitoring electrical activity between the electrode and the penetration wall to develop a signal representing at least one of electrochemical potential, electrochemical impedance, and current passing through the electrolyte between the electrodes and the penetration wall, said electrical activity varying with corrosion of the penetration wall at said distinct positions; and,
   assessing deterioration of the penetration wall as a function of the electrical activity.

2. The method according to claim 1, wherein said electrical activity is monitored during operation of the nuclear reactor pressure vessel.

3. The method according to claim 1, wherein the reactor pressure vessel has a plurality of said penetrations traversing the vessel wall and further comprising selecting from the plurality of penetrations said at least one penetration that is instrumented and estimating corrosion in at least one other of the penetrations from deterioration of the penetration wall adjacent the electrodes.

4. The method according to claim 2, wherein the penetration traverse the reactor pressure vessel at an angle relative to a plane of the reactor pressure vessel at the penetration, whereby the penetration is vulnerable to stress corrosion cracking at an area adjacent the reactor vessel, and further comprising placing the electrodes at least in said area.

5. The method according to claim 1, wherein the penetration comprises a tube attached to the reactor pressure vessel at a substantially circular opening through the vessel wall, and further comprising placing a plurality of electrodes at various positions adjacent discrete areas on at least at one of an internal surface and an external surface of the penetration tube.

6. The method according to claim 5, wherein the tube protrudes internally from the vessel wall and is attached to the vessel wall by welds, and wherein the electrodes are placed in the tube adjacent the welds.

7. The method according to claim 1, further comprising analyzing the signal for a level of electrochemical noise by monitoring for variations in at least one of electrochemical potential and electrochemical current at a range of frequencies.

8. The method according to claim 7, comprising placing at least two said electrodes as a pair in the penetration wall, one of said pair functioning as a reference electrode, and monitoring for variations in said electrochemical potential and said electrochemical current using said at least two electrodes.

9. The method according to claim 1, comprising instrumenting the at least one penetration with an inserted probe having a plurality of electrode pairs, the electrodes in each pair being positioned adjacent one another and close to a distinct area of the penetration wall, each of said electrodes and the penetration wall forming a cell comprising a reference electrode and two working electrodes, and wherein said monitoring and assessing steps include separately monitoring and assessing corrosion in respective distinct areas for each of the cells.

10. A stress-corrosion monitoring apparatus for a nuclear reactor, comprising:
   a reactor vessel arranged to enclose a quantity of nuclear fuel and a coolant forming an electrolyte, the reactor vessel having at least one wall traversed by a plurality of penetrations for coupling external devices to internal structures of the reactor vessel, the penetrations defining conduits and being subjected to stress-corrosion damage due to operation of the nuclear reactor;
   an array comprising a plurality of electrochemical sensors mounted in at least one of the penetrations, the electrochemical sensors each having an electrode insulated from a surface of the at least one of the penetrations and being exposed together with said surface to the electrolyte during operation of the nuclear reactor, said surface and said electrode forming an electrochemical sensing cell wherein said surface functions as a working electrode at a distant area of the surface cooperating with said electrode of the respective electrochemical sensor such that each said electrochemical cell is responsive to localized corrosion of the surface at the distinct area;
   signal conductors coupled to the electrode and to the surface of said at least one of the penetrations, the signal conductors developing voltage and current signals as a function of electrochemical activity leading to the stress-corrosion damage;
   a detector circuit coupled to the signal conductors and being operable to encode data representing at least one of electrochemical potential, electrochemical impedance, and current passing through the electrolyte between the electrode and the surface with said localized corrosion of the surface; and,
   means for reading out said data for assessing deterioration of the penetration wall as a function of the electrochemical activity.

11. The stress-corrosion monitoring apparatus according to claim 10, wherein the at least one penetration traverses a head structure of the reactor pressure vessel.

12. The stress-corrosion monitoring apparatus according to claim 11, wherein the penetration comprises a tubular conduit traversing a wall defined by the head structure of the reactor pressure vessel, the tubular conduit having a longitudinal axis disposed at an acute angle relative to a plane of the wall of the head structure at the penetration, and is attached to the wall of the head structure adjacent an internal end of the penetration, and wherein the array encompasses an area of the tubular conduit at the head structure.

13. The stress-corrosion monitoring apparatus according to claim 12, wherein the penetration is one of a plurality of penetrations of the head structure of the reactor pressure vessel, the penetrations coupling at least one of a control rod positioning mechanism and a sensor signal cable through the head structure to internal structures of the reactor pressure vessel.

14. The stress-corrosion monitoring apparatus according to claim 10, wherein each of the cells comprises a reference electrode and two working electrodes defined by the penetration surface and two said electrodes, positioned to interact through the electrolyte with each said distinct area.

15. The stress-corrosion monitoring apparatus according to claim 14, wherein the electrodes for the respective distinct areas are spaced circumferentially around a sensor probe inserted into the penetration, whereby the sensor signals represent circumferentially spaced areas of the penetration surface.

16. The stress-corrosion monitoring apparatus according to claim 15, wherein the electrodes for the respective distinct areas also are spaced axially on the sensor probe.

17. The stress-corrosion monitoring apparatus according to claim 14, wherein the detector circuit is operable to develop potential noise data from a potential between the penetration surface and one of the electrodes, and current noise data from a current between the penetration surface and another of the electrodes.

* * * * *